(12) United States Patent
Van Bladel et al.

(10) Patent No.: US 10,617,524 B2
(45) Date of Patent: Apr. 14, 2020

(54) TISSUE PROTECTING DEVICES FOR TREATMENT OF CONGESTIVE HEART FAILURE AND OTHER CONDITIONS

(71) Applicant: BioVentrix, Inc., San Ramon, CA (US)

(72) Inventors: Kevin Van Bladel, Livermore, CA (US); Aaron Weiss, San Ramon, CA (US); Lon Annest, New York, NY (US); Gilbert Mata, Jr., New York, NY (US)

(73) Assignee: BioVentrix, Inc., San Ramon, CA (US)

( * ) Notice: Subject to any disclaimer, the term of this patent is extended or adjusted under 35 U.S.C. 154(b) by 370 days.

(21) Appl. No.: 14/835,608

(22) Filed: Aug. 25, 2015

(65) Prior Publication Data
US 2016/0051240 A1    Feb. 25, 2016

Related U.S. Application Data

(60) Provisional application No. 62/041,558, filed on Aug. 25, 2014.

(51) Int. Cl.
*A61F 2/24*    (2006.01)
*A61B 17/04*    (2006.01)
(Continued)

(52) U.S. Cl.
CPC ........ *A61F 2/2487* (2013.01); *A61B 17/0401* (2013.01); *A61B 17/0493* (2013.01);
(Continued)

(58) Field of Classification Search
CPC ............ A61B 17/0401; A61B 17/0493; A61B 2017/00243; A61F 2/2487
See application file for complete search history.

(56) References Cited

U.S. PATENT DOCUMENTS 5,611,354 A     3/1997   Alleyne
6,113,534 A *   9/2000   Koros ................... A61B 17/02
                                                        600/213
(Continued)

FOREIGN PATENT DOCUMENTS

EP    0 606 531 A2    7/1994
EP    2 124 757 A1    12/2009

OTHER PUBLICATIONS

International Search Report and Written Opinion of PCT/US2015/046786 dated Jan. 13, 2016, all pages.

*Primary Examiner* — Christine H Matthews
(74) *Attorney, Agent, or Firm* — Kilpatrick Townsend & Stockton LLP

(57) ABSTRACT

According to one embodiment, a protective device for use in congestive heart failure treatments, and other treatments, includes a control mechanism, an elongate shaft, and a protective plate. The control mechanism is coupled with a proximal end of the elongate shaft and the protective plate is pivotably coupled with a distal end of the elongate shaft. The elongate shaft enables the protective plate to be inserted within a body and navigated distally of a heart wall. The protective plate has a relatively wide and thin body portion and is pivotable relative to the elongate shaft by operation of the control mechanism. Pivoting and/or navigating of the protective plate within the body allows the protective plate to be positioned adjacent the heart wall to shield body organs or tissue surrounding the heart wall from being damaged by surgical instruments inserted through the heart wall.

15 Claims, 11 Drawing Sheets

(51) Int. Cl.
  *A61B 17/00* (2006.01)
  *A61B 17/06* (2006.01)
  *A61B 17/29* (2006.01)

(52) U.S. Cl.
  CPC ........... *A61B 2017/00243* (2013.01); *A61B 2017/0462* (2013.01); *A61B 2017/0464* (2013.01); *A61B 2017/061* (2013.01); *A61B 2017/2927* (2013.01)

(56) References Cited

U.S. PATENT DOCUMENTS

| | | |
|---|---|---|
| 7,662,085 B2 | 2/2010 | Melvin |
| 7,738,968 B2 | 6/2010 | Bleich |
| 8,568,416 B2 | 10/2013 | Schmitz |
| 2001/0025136 A1* | 9/2001 | Leonard ........... A61B 17/00234 600/210 |
| 2005/0240083 A1 | 10/2005 | Orban, III |
| 2007/0255109 A1 | 11/2007 | Stein et al. |
| 2012/0203069 A1 | 8/2012 | Hannaford et al. |
| 2013/0053851 A1* | 2/2013 | Schmitz ............. A61B 10/0275 606/79 |
| 2014/0005666 A1* | 1/2014 | Moua ................. A61B 17/295 606/45 |
| 2015/0174390 A1* | 6/2015 | Nobis ................ A61B 18/1445 606/41 |

* cited by examiner

TISSUE PROTECTING DEVICES FOR TREATMENT OF CONGESTIVE HEART FAILURE AND OTHER CONDITIONS

CROSS-REFERENCES TO RELATED APPLICATION

This application claims the benefit of priority of U.S. Provisional Patent Application No. 62/041,558 filed Aug. 25, 2014, which is herein incorporated by reference in its entirety for all purposes.

BACKGROUND OF THE INVENTION

The present invention is related to improved medical devices, systems, and methods, with many embodiments being particularly useful for reducing the distance between two points in tissue in a minimally or less invasive manner. Specific reference is made to the treatment of a failing heart, particularly the alleviation of congestive heart failure and other progressive heart diseases. The provided devices, systems, and methods will often be used so as to resize or alter the geometry of a ventricle in a failing heart, such as by reducing its radius of curvature through the process of excluding a portion of the circumference from contact with blood, and thereby reduce wall stress on the heart and improve the heart's pumping performance. Although specific reference is made to the treatment of congestive heart failure, embodiments of the present invention can also be used in other applications in which tissue geometry is altered.

Exemplary embodiments described herein provide implants and methods for alleviating congestive heart failure and other progressive diseases of the heart. Congestive heart failure may, for example, be treated using one or more implants which are selectively positioned relative to a first wall of the heart (typically an interventricular septum), and another wall of the heart so as to exclude scar tissue and limit a cross sectional area, or distance across a ventricle. Functional deterioration of the heart tissues may be inhibited by decreasing a size of the heart chamber and/or approximating tissues so that stress on the tissues is limited. Implant locations and overall chamber remodeling achieved by placement of a series of implants may be determined so as to provide a beneficial volumetric decrease and chamber shape.

Congestive heart failure (sometimes referred to as "CHF" or "heart failure") is a condition in which the heart does not pump enough blood to the body's other organs. Congestive heart failure may in some cases result from narrowing of the arteries that supply blood to the heart muscle, high blood pressure, heart valve dysfunction due to degenerative processes or other causes, cardiomyopathy (a primary disease of the heart muscle itself), congenital heart defects, infections of the heart tissues, and the like. However, in many cases congestive heart failure may be triggered by a heart attack or myocardial infarction. Heart attacks can cause scar tissue that interferes with the heart muscle's healthy function, and that scar tissue can progressively replace more and more of the contractile heart tissue. More specifically, the presence of the scar may lead to a compensatory neuro-hormonal response by the remaining, non-infarcted myocardium leading to progressive dysfunction and worsening failure.

People with heart failure may have difficulty exerting themselves, often becoming short of breath, tired, and the like. As blood flow out of the heart decreases, pressure within the heart increases. Not only does overall body fluid volume increase, but higher intracardiac pressure inhibits blood return to the heart through the vascular system. The increased overall volume and higher intracardiac pressures result in congestion in the tissues. Edema or swelling may occur in the legs and ankles, as well as other parts of the body. Fluid may also collect in the lungs, interfering with breathing (especially when lying down). Congestive heart failure may also be associated with a decrease in the ability of the kidneys to remove sodium and water, and the fluid buildup may be sufficient to cause substantial weight gain. With progression of the disease, this destructive sequence of events can cause the progressive deterioration and eventual failure of the remaining functional heart muscle.

Treatments for congestive heart failure may involve rest, dietary changes, and modified daily activities. Various drugs may also be used to alleviate detrimental effects of congestive heart failure, such as by dilating expanding blood vessels, improving and/or increasing pumping of the remaining healthy heart tissue, increasing the elimination of waste fluids, and the like.

Surgical interventions have also been applied for treatment of congestive heart failure. If the heart failure is related to an abnormal heart valve, the valve may be surgically replaced or repaired. Techniques also exist for exclusion of the scar and volume reduction of the ventricle. These techniques may involve (for example) surgical left ventricular reconstruction, ventricular restoration, the Dor procedure, and the like. If the heart becomes sufficiently damaged, even more drastic surgery may be considered. For example, a heart transplant may be the most viable option for some patients. These surgical therapies can be at least partially effective, but typically involve substantial patient risk. While people with mild or moderate congestive heart failure may benefit from these known techniques to alleviate the symptoms and/or slow the progression of the disease, less traumatic, and therefore, less risky therapies which significantly improve the heart function and extend life of congestive heart failure patients has remained a goal.

It has been proposed that an insert or implant be used to reduce ventricular volume of patients with congestive heart failure. With congestive heart failure, the left ventricle often dilates or increases in size. This can result in a significant increase in wall tension and stress. With disease progression, the volume within the left ventricle gradually increases and blood flow gradually decreases, with scar tissue often taking up a greater and greater portion of the ventricle wall. By implanting a device which brings opposed walls of the ventricle into contact with one another, a portion of the ventricle may be excluded or closed off. By reducing the overall size of the ventricle, particularly by reducing the portion of the functioning ventricle chamber defined by scar tissue, the heart function may be significantly increased and the effects of disease progression at least temporarily reversed, halted, and/or slowed.

BRIEF SUMMARY OF THE INVENTION

The present invention generally provides improved medical devices, systems, and methods. Exemplary embodiments of the devices are described for use in reducing the distance between a region along the septum and a region of an external wall of the left ventricle of a heart in a less or minimally invasive manner. According to one embodiment, a tissue/organ protecting device for use in treatment of congestive heart failure is provided. The tissue protecting device includes a control mechanism, an elongate shaft, and a protective plate. The elongate shaft has a proximal end and a distal end. The proximal end of the elongate shaft is coupled with the control mechanism and the distal end of the elongate shaft is pivotably coupled with the protective plate. The elongate shaft is insertable within a body and the distal end of the elongate shaft is advancable distally of a front wall of the heart while the control mechanism is positioned outside of the body. The protective plate has a relatively wide and thin body portion. The protective plate is advancable distally of a rear wall of the heart and pivotable by operation of the control mechanism. Advancement and/or pivoting of the protective plate may be performed to position the protective plate adjacent the rear wall of the heart to shield body organs or tissue surrounding the rear wall from being damaged by surgical instruments inserted through the rear wall.

According to another embodiment, a tissue/organ protecting device is provided. The device includes an elongate shaft having a proximal end and a distal end. The elongate shaft is insertable within a body so that the distal end of the elongate shaft is advancable toward a wall of a heart while the proximal end is positioned outside of the body. The device also includes a protective element that is coupled with the distal end of the elongate shaft. The protective element is positionable adjacent the heart wall to shield body organs or tissue surrounding the heart wall from being damaged by surgical components inserted through the heart wall.

According to another embodiment, a method for treating congestive heart failure is provided. The method includes inserting a protective plate of a protective device within an incision of a body. The protective plate is pivotably coupled with a distal end of an elongate shaft of the protective device. The method also includes advancing the protective plate within the body to position the protective plate distally of a rear wall of a heart and operating a control mechanism to pivot the protective plate relative to the elongate shaft to position the protective plate adjacent the rear wall of the heart. The method further includes inserting a needle through the rear wall of the heart. The protective plate is positioned between the needle and body organs or tissue surrounding the rear wall to shield the body organs or tissue from being damaged by the needle. The method additionally includes inserting an anchor through the rear wall of the heart. The anchor is coupled at a distal end of a tension member that extends through the rear wall of the heart. The method additionally includes tensioning the tension member to engage the anchor with the rear wall and urge the rear wall toward another wall of the heart.

According to another embodiment, a method for protecting body organs or tissue during a surgical procedure is provided. The method includes inserting a protective element of a device within an incision of a body. The protective element is coupled with a distal end of an elongate shaft of the device. The method also includes advancing the protective element within the body and toward a wall of a heart. The method further includes positioning the protective element adjacent the heart wall to shield body organs or tissue surrounding the heart wall from being damaged by surgical components inserted through the heart wall.

BRIEF DESCRIPTION OF THE DRAWINGS

The present invention is described in conjunction with the appended figures.

Figure 1:
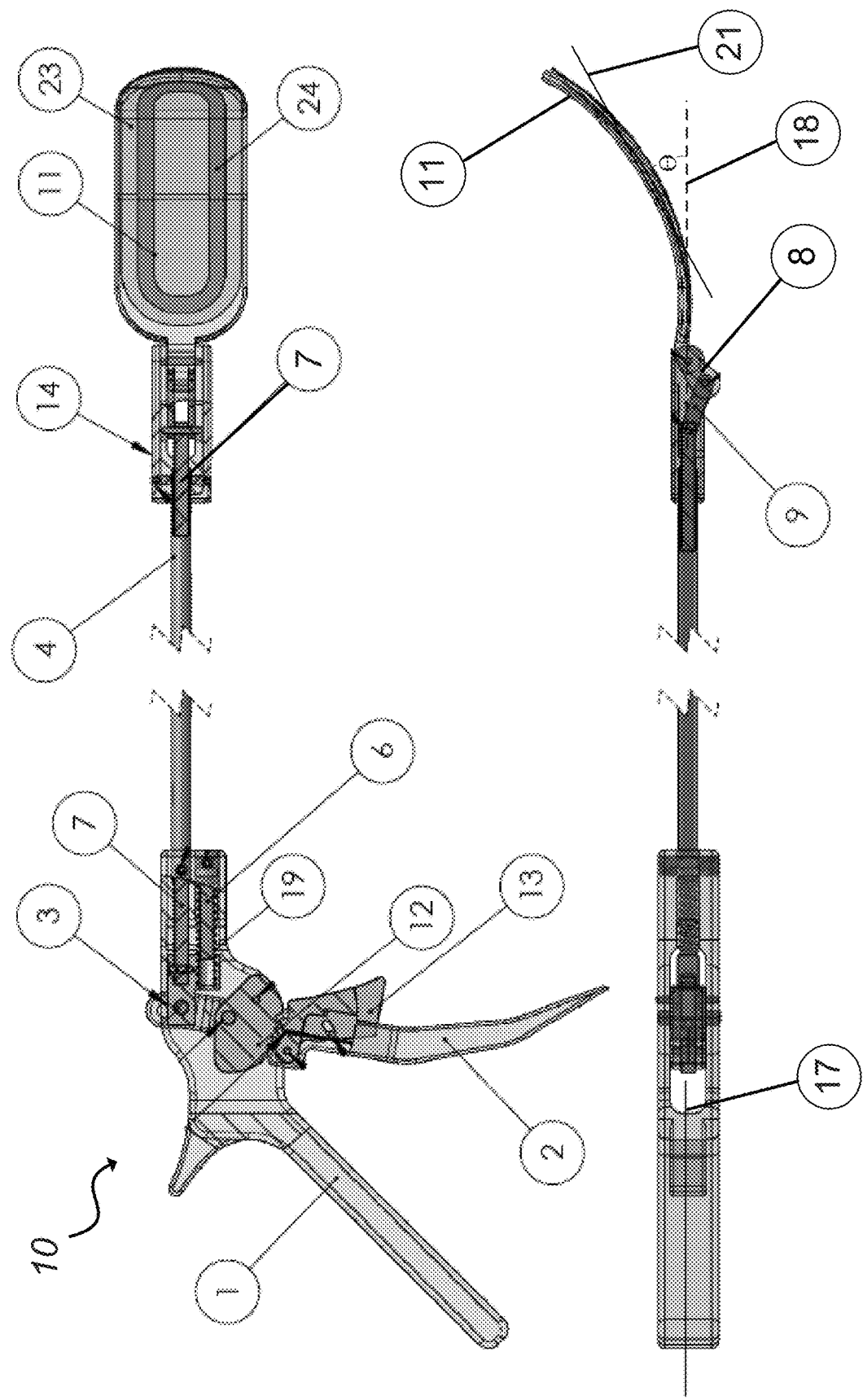
FIG. 1 illustrates a protective device that may be used during treatment of congestive heart failure or for other surgical procedures.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The present invention generally provides improved medical devices, systems, and methods. Exemplary embodiments of the devices are described for use in reducing the distance between a region along the septum and a region of an external wall of the left and/or right ventricle of a heart in a less or minimally invasive manner. Hence, embodiments of the tools and methods described herein may find specific use in the treatment of congestive heart failure and other progressive heart diseases by reconfiguring abnormal heart geometry that may be contributing to heart dysfunction. For congestive heart failure therapies, perforating both the exterior wall and the septum from an epicardial approach can provide significant benefits in control over the locations of implant deployments, thereby effectively enhancing the resulting reshaping of the ventricular chamber.

In performing congestive heart failure treatments or surgical procedures, a guidewire and one or more heart anchors may be used. The guidewire is often inserted through one or more external walls and the septal wall of the heart. The external walls and/or septal wall are often composed of relatively tough scar tissue, which makes insertion of the guidewire through these walls relatively challenging. Relatively thin and long needles (e.g., 17 Gauge (0.058")) are often used to penetrate the scar tissue of the external and/or septal walls. The needles need to be relatively long to allow a physician to position the needle through a small incision, through the external and/or septal walls. In some embodiments, the needle may be penetrated through a front external wall, through the septal wall, and through a rear external wall. In other embodiments, the needle may be inserted through the septal wall and through the rear external wall. As used herein, the term front external wall refers to the heart wall that is positioned near and faces an individual's chest and rib cage. The term rear external wall refers to the heart wall positioned opposite the front wall, or positioned near and facing an individual's back.

Since congestive heart failure treatments or surgical procedures are often performed via incisions within or near the patient's chest, inserting the needle, or other surgical instrument, through the rear heart wall often expose the distal end of the needle or surgical instrument to body organs and/or tissue positioned behind and/or surrounding the rear heart wall. Extreme care and precaution needs to be taken as the needle, or other surgical instrument, is penetrated through the rear external wall since the sharp distal end of the needle is exposed to the surrounding body organs and/or tissue. If the needle or surgical instrument contacts and/or penetrates the surrounding body organs and/or tissue, the organs/tissue may be damaged and the patient may experience unnecessary trauma and/or bodily injury.

The protective devices described herein are able to protect against such organ/tissue damage by shielding the surrounding organs and/or tissue from the distal end of the needle and/or other surgical instrument. The protective devices include a body portion that is impenetrable by the needle and/or other surgical instruments. The body portion of the protective device is positionable between the needle/surgical instrument and the surrounding organs/tissue and functions as a barrier to prevent contact with, and damage to, the surrounding organs/tissue. The protective devices include an elongate shaft that allows a physician to insert the body portion within the incision and to navigate the body portion adjacent the heart wall. In some embodiments, the body portion may be pivoted relative to the shaft and relative to the heart wall. Pivoting of the body portion allows the body portion to be positioned behind the surface of the rear heart wall. In this manner, organs/tissue positioned behind the rear heart wall surface may be protected even though the surgical instruments are being inserted within the body through incisions near the chest. In a specific embodiment, the body portion may be positioned behind an apical portion of the heart and the needle, or other surgical instrument, may be inserted through the rear heart wall near the heart apex.

The protective devices typically include a control mechanism that controls pivoting of the body portion. In some embodiments, the control mechanism includes a handle and trigger mechanism that may be operated with a single hand. Operating the trigger mechanism causes an inner shaft that is disposed within a lumen of the elongate shaft to slide proximally and distally within the elongate shaft's lumen. Distal sliding of the inner shaft causes the body portion to pivot, whereas proximal sliding of the inner shaft causes the body portion to return to an un-pivoted positioned.

For convenience in describing the embodiments herein, the description will mainly refer to the protective devices protecting body organs that surround and/or positioned adjacent the heart. It should be realized, however, that body tissue may also be protected by the protective devices and that the devices are not limited to protecting body organs only. Further, the description will mainly refer to the protective devices protecting the body organs/tissue from contact by and/or damage from needles. It should be realized, however, that the protective devices are capable of protecting the body organs/tissue from contact with and/or damage from other surgical instruments, such as catheters, heart anchors, and the like. Similarly, although the embodiments generally refer to the protective devices being used with the heart during congestive heart failure treatments, it should be realized that the protective devices may be used elsewhere within the body, and/or for other treatments, to protect tissue and/or body organs. As such, the use of the protective devices is not limited to the heart.

Having described several aspects and features of the protective devices generally, additional aspects and features will be recognized with reference to the description of the several embodiments provided hereinbelow.

Referring now to FIG. 1, illustrated is an embodiment of a protective device 10 that may be used in treatment of congestive heart failure and/or other surgical procedures. Protective device 10 includes a control mechanism 1, which in the illustrated embodiment is a handle (hereinafter handle 1). The handle 1 may be gripped by a user to control the protective device 10 and/or move a protective element 11, which in the illustrated embodiment is a plate having an arcuate or crescent shape configuration (hereinafter protective plate 11). The handle 1 is connected to a proximal end of an elongate rod 4 while the protective plate 11 is coupled with a distal end of the elongate rod 4. The elongate rod 4 is typically a small diameter and relatively long shaft that enables the protective plate 11 to be inserted and navigated within a patient's body while the handle 1 remains outside the patient's body and under control of a physician. The small diameter shaft of the elongate rod 4 minimizes contact of the rod 4 with various body organs as the protective plate 11 is inserted and navigated within the patient's body. In contrast, the protective plate 11 has a relatively wide and thin body portion. The wide configuration of the body portion provides a large surface area that shields body organs adjacent the heart from being contacted by various surgical instruments that are inserted through the heart as described herein. The thinness of the body portion reduces the contact of the protective plate 11 with body tissue and/or organs as the protective plate 11 is navigated within the patient's body, thereby aiding insertion of the protective plate 11 within the body. In some embodiments a surface of the protective plate 11 may have a continuous curve surface. In other embodiments, the surface of the protective plate 11 may have a planar portions or region and a curved or arcuate portion or region. In such embodiments, the surface may be a curved planar surface wherein the surface curves in two dimensions (e.g., the surface curves in the dimensions orthogonal to an axis through the sheet), but does not curve in a third dimension. In other embodiments, the surface may curve in three dimensional space, such as by having a concave or convex dome shape.

In operation, the protective plate 11 is navigated through an incision within the body and toward the patient's heart. The protective plate 11 is positioned adjacent the patient's heart and forms a protective barrier between one or more body organs surrounding and positioned adjacent the patient's heart and surgical components, such as a needle, that are inserted through a wall of the heart. For example, as a needle is inserted through the heart wall, the needle contacts the protective plate 11 and is unable to penetrate through the protective plate 11 and into contact with one or more body organs positioned behind the protective plate 11. In this manner, the protective plate 11 shields the organs from damage that otherwise may occur as the needle is penetrated through the heart wall and/or advanced distally of the heart.

To facilitate positioning of the protective plate 11 adjacent the heart, the protective plate 11 has an arcuate configuration that more closely conforms to the shape of the heart. Further, the protective plate 11 is pivotably coupled with the distal end of the elongate shaft 4 to allow the protective plate 11 to pivot relative to the elongate shaft 4 and the patient's heart. The protective plate 11 is pivotable from a first position in which the main body of the protective plate 11 is roughly aligned with an axis 18 of the elongate shaft 4 to a second position in which the main body of protective pate 11 is angled relative to the axis 18 of the elongate shaft 4. As used herein, reference to the protective plate's main body being roughly aligned with the axis 18 of the elongate shaft 4 means that a plane 21 that is roughly aligned with the protective plate's main body is aligned with the elongate shaft's axis 18, or forms a relatively small angle θ with the axis 18 of less than about 15 or 20 degrees. Similarly, as used herein, reference to the protective plates main body being angled relative to the axis 18 of the elongate shaft 4 means that the plane 21 forms an angle θ with the axis 18 of more than about 15 or 20 degrees.

Pivoting of the protective plate 11 allows the protective plate 11 to be positioned behind the rear wall or surface of the heart. Since surgical instruments are often inserted through frontal body incisions in performing congestive heart failure treatments and other treatments, accessing the rear heart wall is often a challenge and/or requires gripping and moving the heart. In contrast, since the protective plate 11 is able to pivot relative to the elongate shaft 4, the protective plate 11 may be easily positioned behind the heart's rear wall from a frontal body incision without moving the heart, or while minimizing the amount of heart movement required. Positioning of the protective plate 11 behind the heart's rear wall is achieved by pivoting the protective plate into position behind the rear wall, such as during, or subsequent to, movement of the protective plate 11 toward the heart. Pivoting the protective plate 11 behind the heart's rear wall essentially cups the protective plate 11 around a portion of the heart's rear wall or surface.

To enable pivoting of the protective plate 11 relative to the elongate shaft 4, a coupling component 14 is connected to a distal end of the elongate shaft 4 and to the protective plate 11. A proximal end of the protective plate 11 is coupled with a coupling component 14 via a pin (not numbered) that is inserted through corresponding apertures of the coupling component 14 and protective plate 11. An arm 8 of the protective plate 11 extends proximally from the pin and couples with a strut 9 via a second pin (not numbered) that is inserted through corresponding apertures of the arm 8 and strut 9. The proximal end of the strut 9 is coupled with an inner or actuating rod 7 that is disposed within a lumen of the elongate shaft 4. Distal movement of the actuating rod 7 within the lumen of elongate shaft 4 causes the strut 9 to press against the arm 8, which causes the protective plate 11 to pivot about the pin coupling the protective plate 11 with the coupling component 14. Similarly, proximal movement of the actuator rod 7 within the lumen of elongate shaft 4 pulls on the strut 9, which in turn pulls on arm 8 and causes the protective plate 11 to pivot in an opposite direction about the pin coupling the protective plate 11 with the coupling component 14. In this manner, the protective plate 11 is pivotable from the first position to the second position described previously.

A proximal end of the actuating rod 7 is coupled with a lever mechanism or trigger 2, which is pivotably coupled with the handle 1. The lever mechanism or trigger 2 may be grasped by a user and pulled or pivoted relative to handle 1, which causes the actuating rod 7 to move proximally and distally within the lumen of elongate shaft 4, and thereby pivot protective plate 11. The protective device 10 is configured so that a user may grasp the handle 1 and the lever mechanism 2 with a single hand and pivot protective plate 11. The lever mechanism 2 is biased toward a non-pivot position in which the protective plate 11 is positioned in the first position described above—i.e., the plane 21 forms a relatively small angle θ with the axis 18 of elongate shaft 4. The lever mechanism 2 is biased toward this position via a spring 6 that is positioned within a recess near the distal end of handle 1. The spring 6 presses against a small shaft 19, which in turn presses against lever mechanism 2 and causes the lever mechanism 2 to return to the non-pivot position.

In some embodiments, the protective device 10 may include a stop component 3 that functions as a limit or stop for the pivoting of protective plate 11. The stop component 3 may limit pivoting of the protective plate 11 by preventing lever mechanism 2 from being actuated beyond a set amount or degree. In some embodiments, stop component 3 includes a wall of a slot or recess within which a top portion of the lever mechanism 2 moves as lever mechanism 2 is pivoted relative to handle 1. Contact between the top portion of the lever mechanism 2 and the wall of the slot or recess prevents further pivoting of the lever mechanism 2 relative to handle 1, which in turn prevents further pivoting of protective plate 11. In some embodiments, the stop component 3 may be adjustable to vary a stop point or position of the lever mechanism 2.

In some embodiments, protective device 10 includes a locking mechanism that functions to lock the protective plate 11 in a pivoted configuration, such as in the second position described previously. As illustrated in FIG. 1, the locking mechanism includes a cam component 12 having a plurality of teeth positioned on a bottom cam surface. The teeth of cam component 12 lockingly engage with corresponding teeth of a lock member 13. Cam component 12 is fixedly coupled with handle 1 while lock member 13 is pivotally coupled with lever mechanism 2. Pivoting of the lever mechanism 2 relative to handle 1 causes the teeth of lock member 13 to pivot into engagement with the teeth of cam member 12 in a ratchet like manner. Upon release of the lever mechanism 2, the engaged teeth of lock member 13 and cam member 12 hold or otherwise maintain the lever mechanism 2 and handle 1 in a pivoted configuration. The protective plate 11 is likewise held or maintained in a pivoted configuration relative to elongate shaft 4.

The plurality of teeth of lock member 13 and cam component 12 allow the lever mechanism 2 and handle 1 to be incrementally locked in numerous pivoted configurations, which allows the protective plate 11 to likewise be incrementally locked in numerous pivoted configurations or positions relative to elongate shaft 4. In this manner, a desired fit or arrangement of protective plate 11 about the patient's heart may be achieved by actuating lever mechanism 2 and locking lever mechanism 2 and protective plate 11 in the desired fit/arrangement. The lever mechanism 2 may be unlocked from handle 1 by pressing on lock member 13, which causes the lock member 13 to pivot relative to lever mechanism 2 and causes the teeth of lock member 13 and cam component 12 to disengage.

The protective plate 11 is typically made of a hard and impenetrable material, such as metal, plastic, and the like. The material of protective plate 11 is typically also non-toxic to the human body since the protective plate 11 will be inserted and used within the body. For example, the protective plate 11 may be made of stainless steel and/or similar materials. In some embodiments, protective plate 11 includes one or more material layers. For example, protective plate 11 may include a first material layer 23 and a second material layer 24 that are coupled, bonded, or otherwise attached together. The various material layers, 23 and 24, may provide one or more functions for protective plate 11, such as allowing the protective plate 11 to be easily inserted and positioned within the body and adjacent the heart.

In some embodiments, the protective plate 11 is roughly aligned with the handle 1. As used herein, reference to the protective plate 11 being roughly aligned with the handle 1 means that the plane 21 of protective plate 11 is roughly aligned with a plane 17 of handle 1, or forms a relatively small angle θ with plane 17 of less than about 15 or 20 degrees. In such a configuration the handle 1 and protective plate 11 are roughly aligned on opposite ends of the elongate shaft 4. Aligning of the handle 1 and the protective plate 11 facilitates navigating the protective plate 11 within the body and positioning the protective plate 11 adjacent the heart by aligning the physician's palm with the protective plate 11. For example, the protective plate is often positioned around the heart's apex, with the elongate shaft 4 positioned below or adjacent the apex and the protective plate 11 pivoted to extend upward from near the apex and behind the rear wall or surface of the heart. Since the physician's palm is aligned with the protective plate 11, the physician's palm is in a more natural position relative to the patient—i.e., roughly perpendicular to the patient's body—as the protective plate 11 is navigated and positioned about the heart. In other embodiments, the protective plate 11 and handle 1 may not be aligned. For example, in other embodiments, the plane 21 of the protective plate 11 and the plane 17 of the handle 1 may be roughly perpendicular.

Figures 2A, 2B:
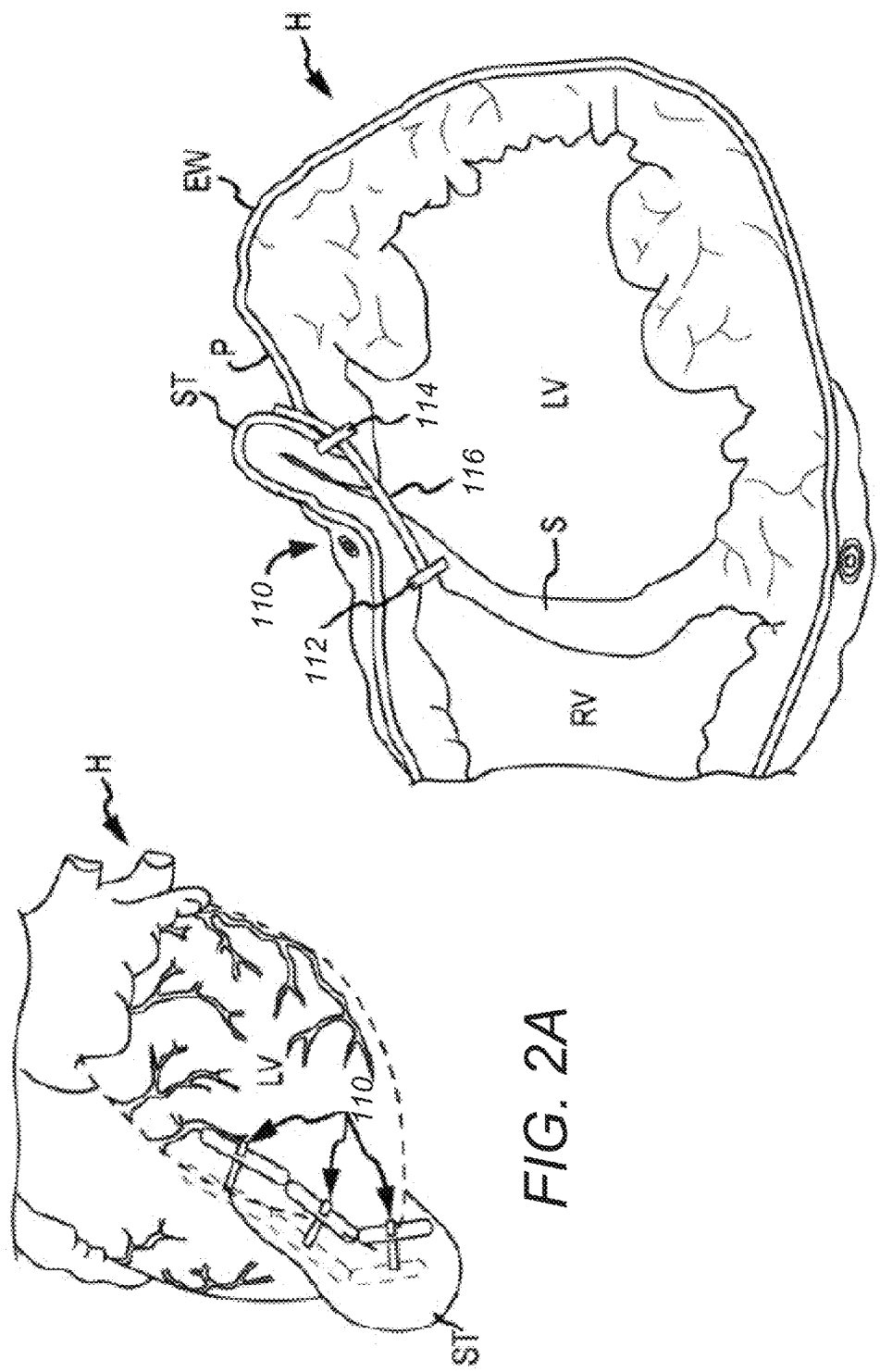
FIG. 2A illustrates a reconstructed left ventricle using a series of implanted anchors so as to mitigate the deleterious effects of congestive heart failure.
FIG. 2B illustrates a cross-sectional view of the heart of FIG. 2A, showing a reduction in the size of the left ventricle effected by one of the implants.

Referring now to FIGS. 2A-5G, procedures for treating congestive heart failure using the tissue protecting device 10 are illustrated. Specifically, FIGS. 2A and 2B illustrate a series of implants 110 implanted in a heart H so as to decrease a cross-section of a left ventricle LV. Each implant 110 generally includes a first anchor 112, a second anchor 114, and a tension member 116 coupling the anchors together. Tension in the tension member 116 is transferred from the anchors, 112 and 114, to the septum S and the external wall EW bordering the left ventricle LV so as to bring these structures into engagement, thereby effectively excluding a region of scar tissue ST from the left ventricle. In many embodiments described herein, implant 110 will be deployed by penetrating the external wall EW and septum S via a pericardium P of the heart H, and also by accessing a right ventricle RV via a right atrium. In other embodiments illustrated herein, one or more anchors may be engaged with an external wall EW of the right ventricle RV. Anchors deployed within a right ventricle and/or in engagement with the septum S may sometimes be referred to herein as septal anchors, while anchors deployed along the external wall EW of the left ventricle LV and/or right ventricle RV may be referred to as epicardial anchors.

Figure 2C:
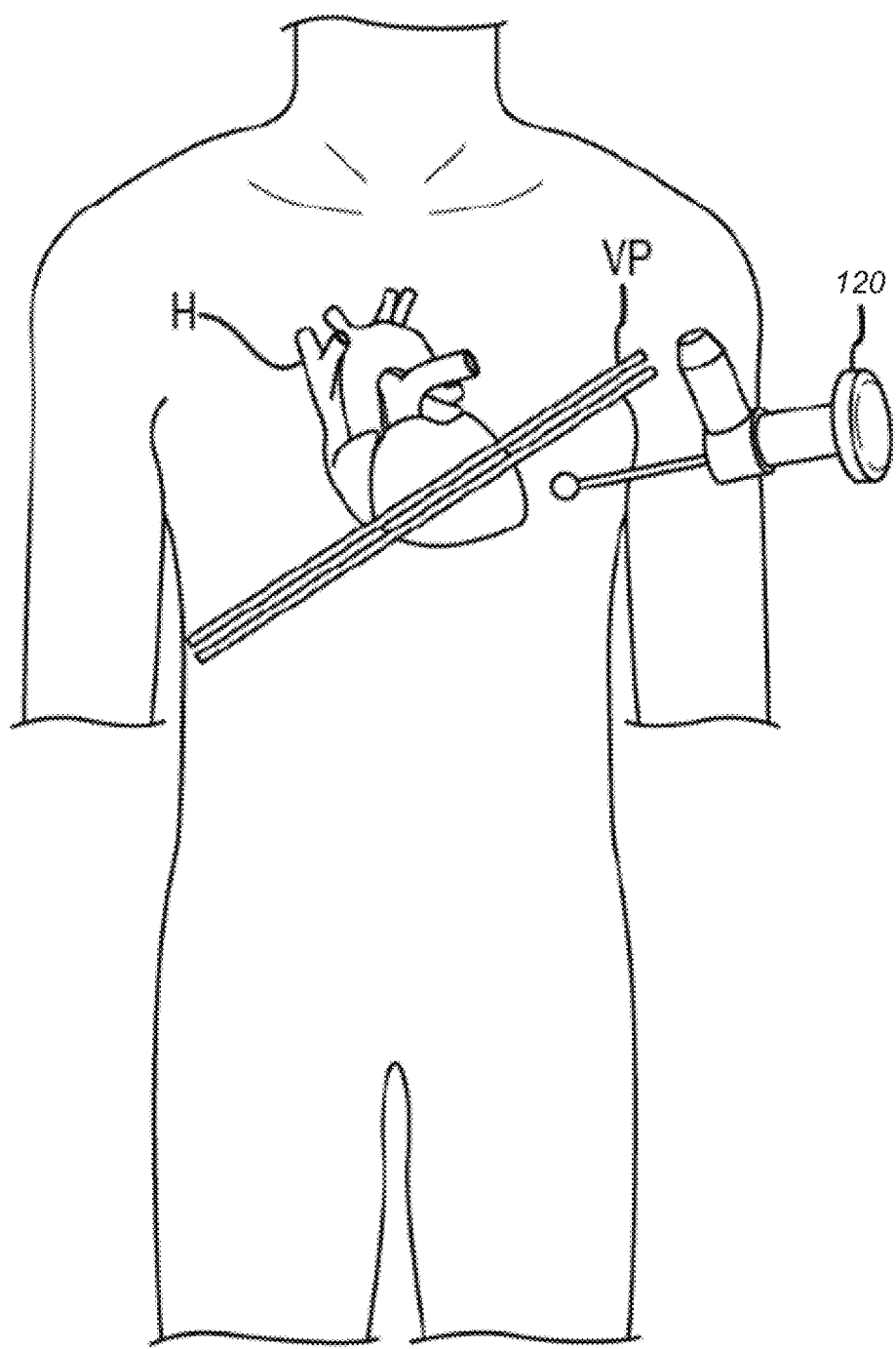
FIGS. 2C and 2D illustrate minimally invasive access to and endoscopic imaging of a pericardium of the heart.
Figure 2D:
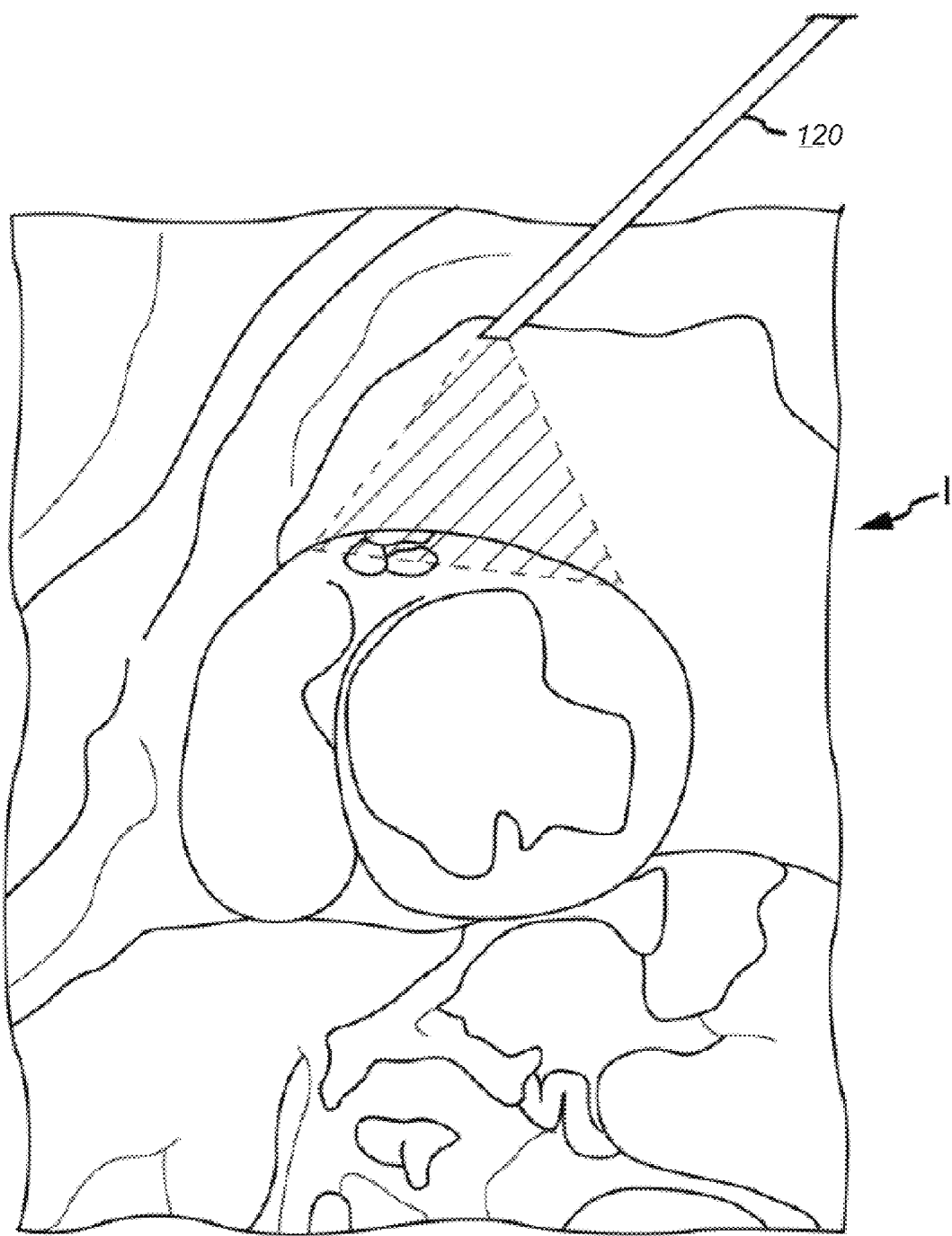

Referring now to FIGS. 2C and 2D, an MRI image I taken along viewing plane VP schematically illustrates use of a thoracoscope or fluoroscope 120 to provide a field of view encompassing a region of the pericardium of the heart, with the region including a target site for deployment of one or more epicardial anchors and/or septal anchors of the implant system.

Figure 3A:
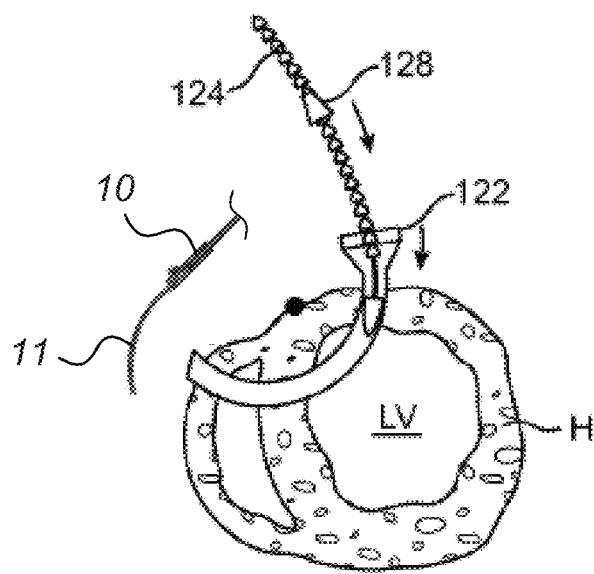
FIGS. 3A-3C schematically illustrate one variation of a transventricular implant and anchor system from a left ventricular approach.
Figure 3B:
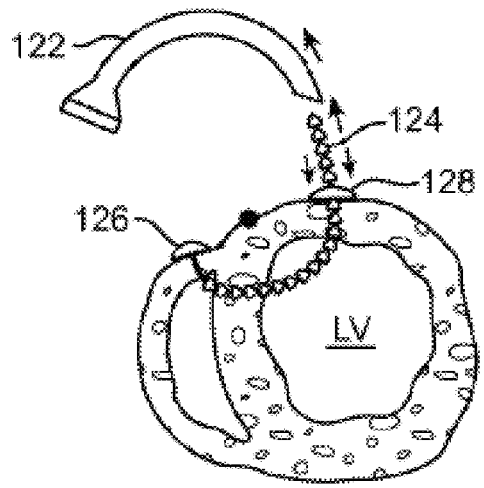
Figure 3C:
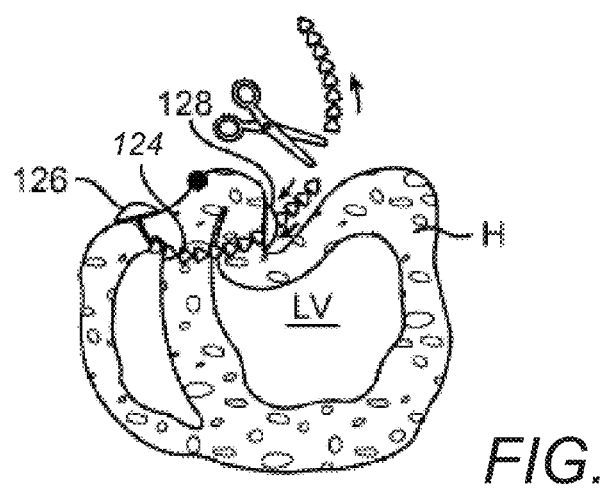

With reference to FIGS. 3A-3C, illustrated is an embodiment of a transventricular implant and anchor system deployment from a left ventricular LV approach. A sharpened, curved tissue piercing tubular body or needle 122 pierces the left ventricular wall, the septum, and extends back out through the right ventricular wall. The protective device 10 is positioned adjacent the right ventricular wall and between the tubular body or needle 122 and body organs or tissue surrounding the right ventricular wall. The protective device 10 prevents the sharpened distal end of tubular body 122 from piercing the surrounding body organs and/or tissue and, thus, shields the body organs/tissue from unintentional and undesired damage. If the tubular body 122 is extended sufficiently beyond the right ventricular wall, the tubular body 122 will contact the protective plate 11 of protective device 10, which as described above is a relatively impenetrable barrier. To access and position the protective plate 11 adjacent the right ventricular wall, the protective plate 11 is typically navigated to near the penetration site or location and the protective plate pivoted so as to be adjacent the penetration site. In some embodiments, the protective plate 11 may be incrementally pivoted as the protective plate 11 is navigated through the body. In this manner, the protective plate 11 may incrementally curve around the heart while being inserted within the body.

With the tubular body 122 inserted through the left ventricular wall, septum, and right ventricular wall, a ratcheted tension member 124 is introduced through the tissues of the heart within a lumen of tubular body 122. A first anchor 126 is attached to the tension member 124. The first anchor 126 is expanded or affixed to the right ventricular wall after the first anchor 126 is inserted through the tubular body 122 and the distal end of the tension member 124 extends free of the heart tissue. Once the tension member 124 extends into and/or through both ventricles, the tubular body 122 can be withdrawn proximally and a second anchor 128 can be moved distally along the tension member 124 to engage the myocardial surface of the heart (i.e., left ventricular wall), as seen in FIG. 3B. Second anchor 128 may optionally pass through the lumen of tubular body 122 and expand radially, or may be coupled to tension member 124 after the tubular body 122 is withdrawn.

An exemplary ratcheting interface between tension member 124 and second anchor 128 may make use of a series of radial protrusions and/or detents disposed along an axis of the tension member. For example, the tension member 124 may have slide surfaces which taper radially outwardly distally along the tension member 124 to allow the anchor 128 interface to slide sequentially over the slide surfaces in a distal direction, and detent surfaces which are oriented distally to engage corresponding proximally oriented surfaces of the anchor 128 interface so as to inhibit proximal movement of the anchor relative to the tension member 124. Second anchor 128 may have a ratchet interface structure including (or derived from) the sealing components of a Touhy-Borst valve structure. Such an interface may resiliently deflect to pass the slide surfaces of the tension member 124 and may grab or engage the detent surface when the tension member 124 is pulled distally. Such a valve structure may also be increased in diameter to release the tension member if desired and/or tightened towards its smallest diameter to immovably (and optionally permanently) affix the anchor 128 relative to the tension member 124. Exemplary embodiments of ratcheting tension member 122 may comprise polymers or metals, optionally comprising a polyester such as Mylar®, a thermoplastic such as Nylon™, a stainless steel, a shape memory allow such as Nitinol™, or the like.

As shown in FIG. 3C, second anchor 128 can be positioned along tension member 124 so as to effectively exclude scar tissue from the left ventricle and/or reduce a volume of the left ventricle. Some portion of tension member 124 may be disposed within the right ventricle, right ventricle scar tissue may be excluded, and/or the volume of the right ventricle may also be reduced. The tension member 124 may be severed using a blade or the like as shown schematically, though some of the tension member 124 may extend into the extracardiac space. In alternative embodiments using different surgical approaches, at least a portion of the tension member may extend into the right ventricle or the like.

Figure 4A:
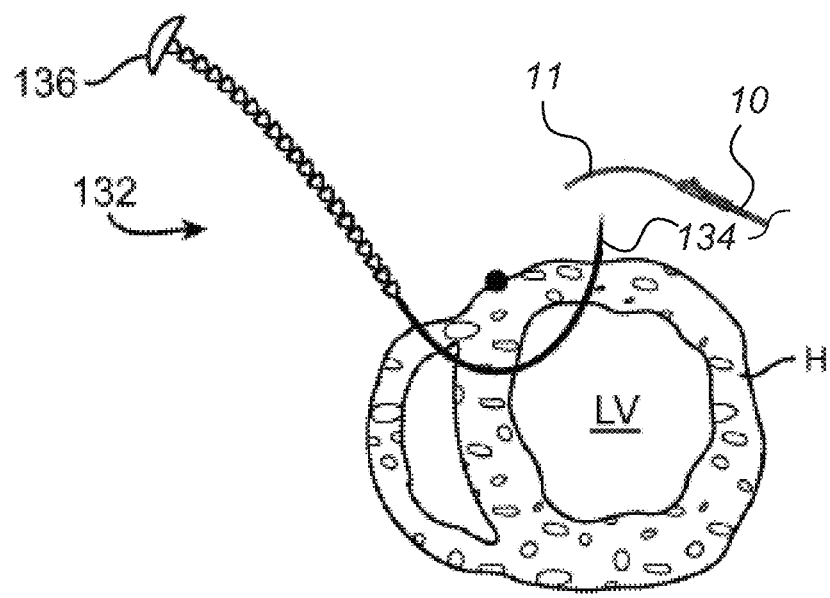
FIGS. 4A and 4B schematically illustrate another variation of a transventricular implant and anchor system from a right ventricular approach.
Figure 4B:
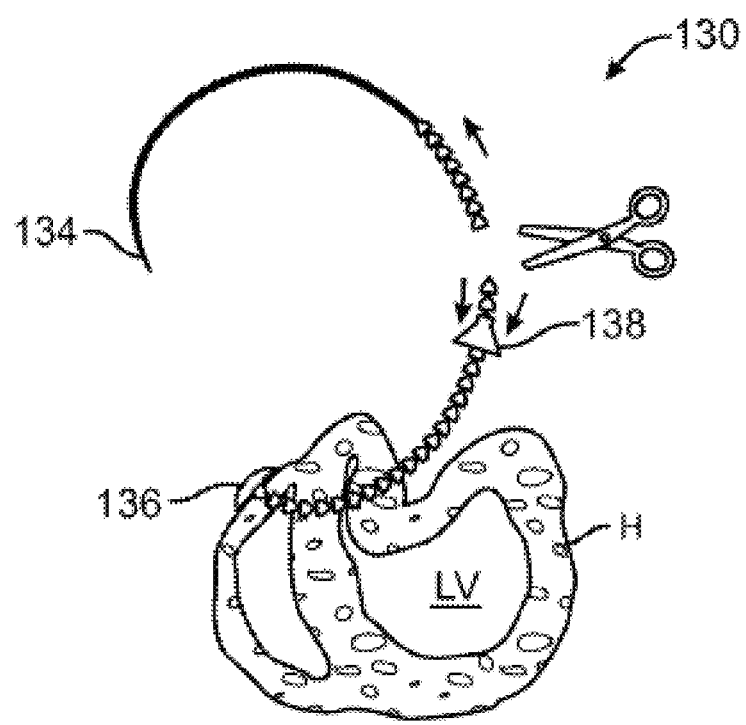

Referring now to FIGS. 4A and 4B, another alternative embodiment of an implant 130 and deployment system makes use of a transventricular approach from the right ventricle. A curved tension member 132 having a distal tissue penetrating end or needle 134 and a proximal anchor 136 affixed thereto is introduced through the wall of the right ventricle, through the septum, across the left ventricle LV, and out through the left ventricular wall. The protective device 10 is positioned adjacent the left ventricular wall between the tissue penetrating end 134 and the body organs or tissue surrounding the left ventricular wall. The protective device 10 shields the surrounding body organs and/or tissue from contact by and/or damage from tissue penetrating end 134. Extension of the tissue penetrating end 134 sufficiently beyond the left ventricular wall causes the tissue penetrating end 134 to contact protective plate 11 and not the surrounding body organs and/or tissue. As described previously, protective plate 11 is positioned adjacent the left ventricular wall by navigating and/or incrementally pivoting protective plate 11 as needed.

The tension member 132 and affixed anchor 136 are advanced distally so that the anchor 136 engages the surface of the heart, and a second anchor 138 is attached by passing distal end 134 through the anchor. Second anchor 138 is ratcheted proximally along tension member 132 to exclude scar tissue and limit a size of the left ventricle, with the distal end and at least a portion of the tension member that is distal of the positioned anchor being severed and removed from the deployed implant. In some embodiments, protective device 10 may be used as the tissue penetrating end 134 is advanced distally of the left ventricular wall to ensure that the surrounding body organs and tissue are shielded from the tissue penetrating end 134.

Figure 5A:
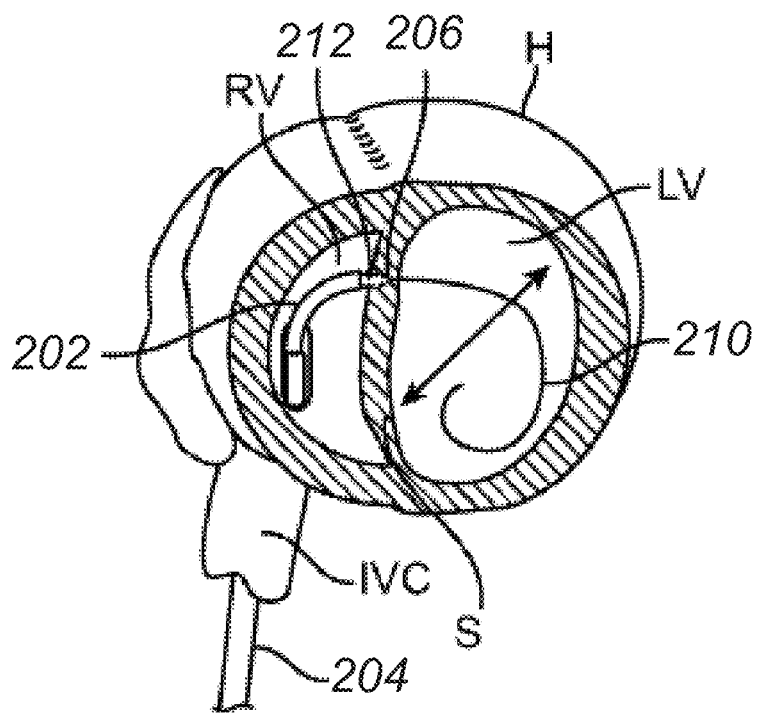
FIGS. 5A-5G schematically illustrate another variation of a transventricular implant and anchor system from a right atrium approach.

With reference to FIGS. 5A-5G, illustrated is an embodiment of a transventricular implant and anchor system deployment from a right atrium approach. FIG. 5A shows a transverse cross-sectional or four-chamber view of heart H. A guidewire 210 and a dilator 212 are advanced through second catheter sheath 202, which may be disposed within a first catheter sheath 204. Guidewire 210 is used to perforate the septum S, preferably a dysfunctional area of the septum S, for example, by using radiofrequency (RF) energy and the like. In other embodiments, a needle (not shown) may be used to penetrate the septum S and then guidewire 210 may be advanced through the penetration created by the needle. Guidewire 210 is then advanced and coiled in the left ventricle LV. Dilator 212 has a tapered distal end 206 that facilitates in advancing the dilator 212 across the septum S.

Figure 5B:
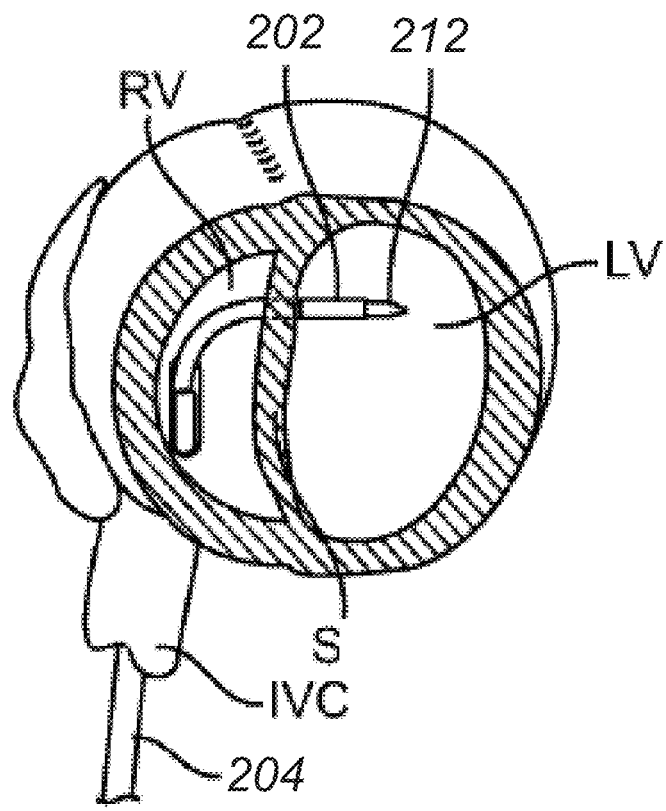
Figure 5C:
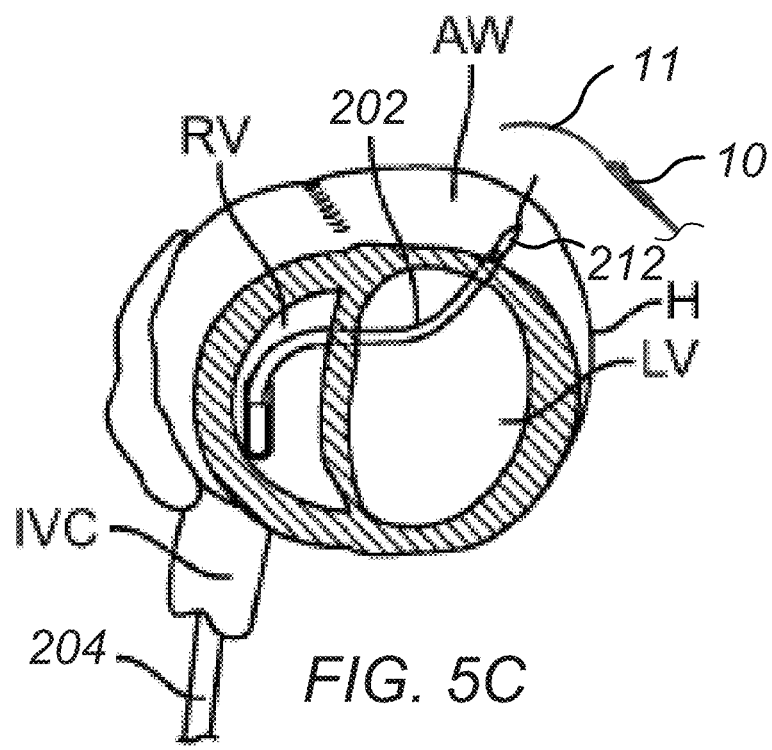

FIG. 5B shows a cross-sectional view of the heart H with dilator 212 advanced through the septum S and into the left ventricle LV through the perforation made by guidewire 210 and/or a needle (not shown). FIG. 5C shows a cross-sectional view of the heart H as dilator 212 is advanced through the anterior wall of the left ventricle LV. In some embodiments, the guidewire 210 is used to perforate the anterior wall of the left ventricle LV, for example, by using radiofrequency (RF) energy. In other embodiments, a needle or other tissue penetrating device is used to perforate the anterior wall of the left ventricle. After dilator 212 has advanced through the anterior wall of the left ventricle LV, the second catheter sheath 202 may be advanced through the anterior wall AW of left ventricle LV. The protective device 10 is positioned adjacent the anterior wall of the left ventricle LV between the tissue penetrating device (e.g., the guidewire 210, the needle, dilator 212, etc.) and the body organs or tissue surrounding the left ventricular wall. The protective device 10 shields the surrounding body organs and/or tissue from contact by and/or damage from tissue penetrating devices. For example, the protective device 10 may shield the surrounding body organs/tissue from the RF energy of the guidewire 210 and/or shield the surrounding body organs/tissue from the sharp distal tip of the needle and/or dilator 212. As described previously, the protective plate 11 is positioned adjacent the anterior wall of the left ventricle LV by navigating and/or incrementally pivoting protective plate 11 into position.

Figure 5D:
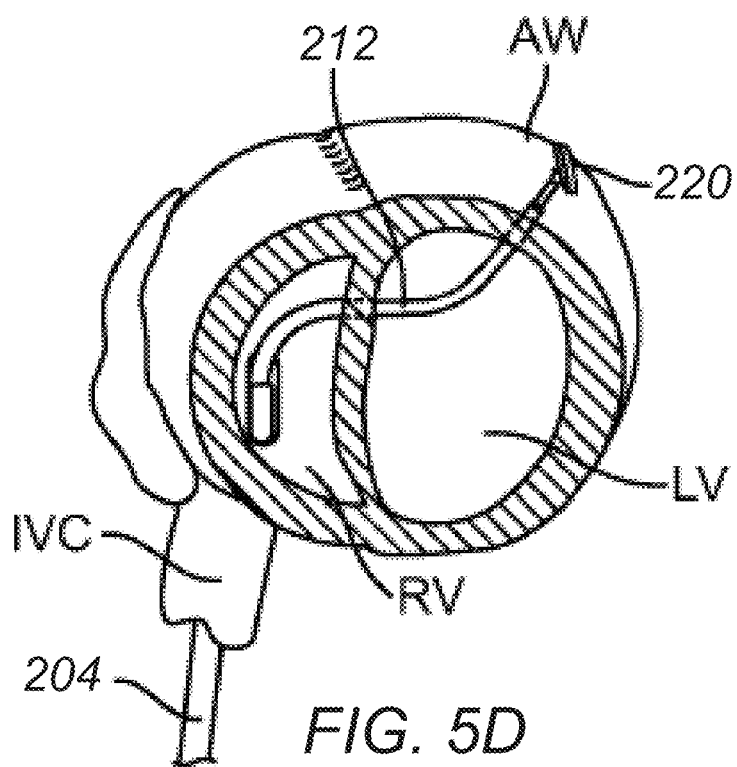

After the guidewire 210, dilator 212, and second catheter sheath 202 are advanced through the anterior wall of the left ventricle LV, the guidewire 210 and dilator 212 are retrieved, leaving second catheter sheath 202 positioned through the anterior wall AW of the left ventricle LV. An anchor assembly 220 (i.e., an epicardial anchor and tether T) may then be inserted within a lumen of the second catheter sheath 202 and pushed or advanced to the distal end of the second catheter sheath 202. In this manner, the epicardial anchor 220 is delivered to the epicardium of the anterior wall of left ventricle LV. FIG. 5D shows that the epicardial anchor 220 is then aligned along about the epicardium, such as along the long axis of the heart. As shown in FIG. 5D, tension can then be applied to tether T (see FIG. 5E) to position epicardial anchor 220 against the epicardium.

Figure 5E:
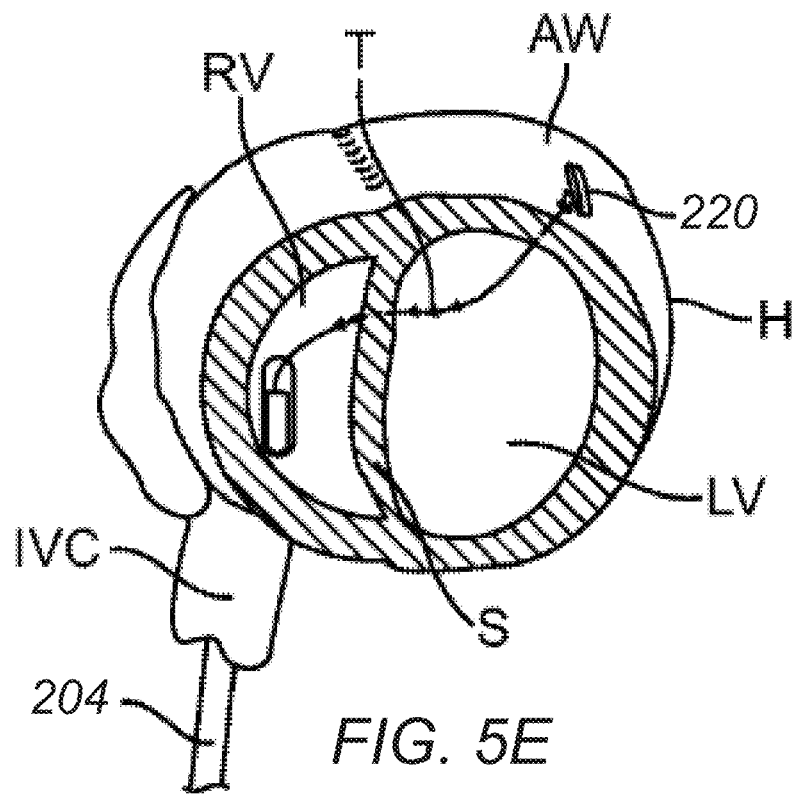
Figure 5F:
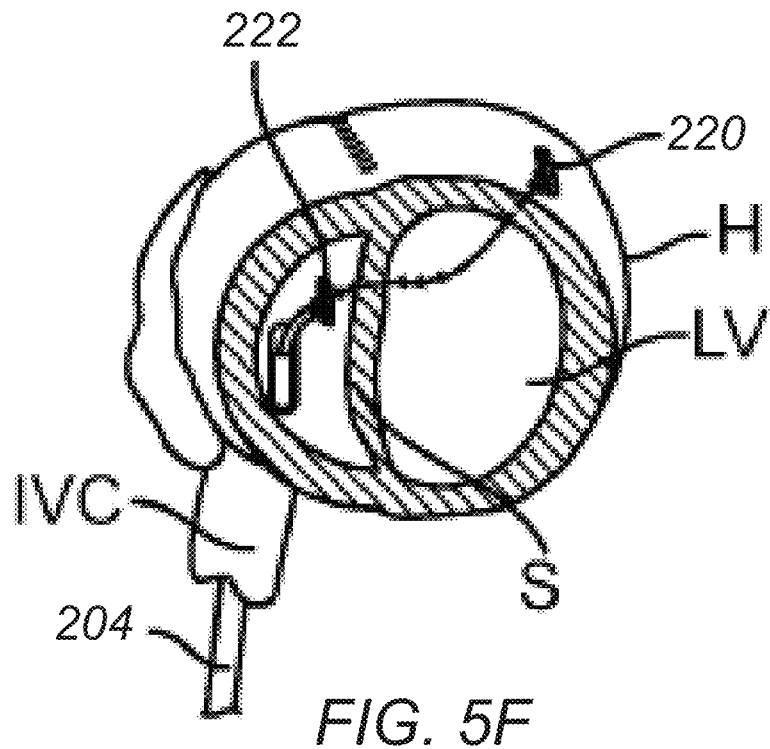

FIG. 5E shows a cross-sectional view of the heart H as second catheter sheath 202 is retrieved or removed from the left ventricle LV via a lumen of first catheter sheath 204. A septal or external anchor 222 (see FIG. 5F) may then be loaded into a proximal end of first catheter sheath 204 over tether T of anchor assembly 220. As shown in FIG. 5F, septal anchor 222 is then deployed against the septum S in the right ventricle RV, for example, by means of a push catheter (not shown). A locking mechanism (not shown) can then be introduced through first catheter sheath 204 and advanced against septal anchor 222 to lock the septal anchor 222 and epicardial anchor 220 about tether T and in engagement with the septum S and left ventricle LV respectively.

Figure 5G:
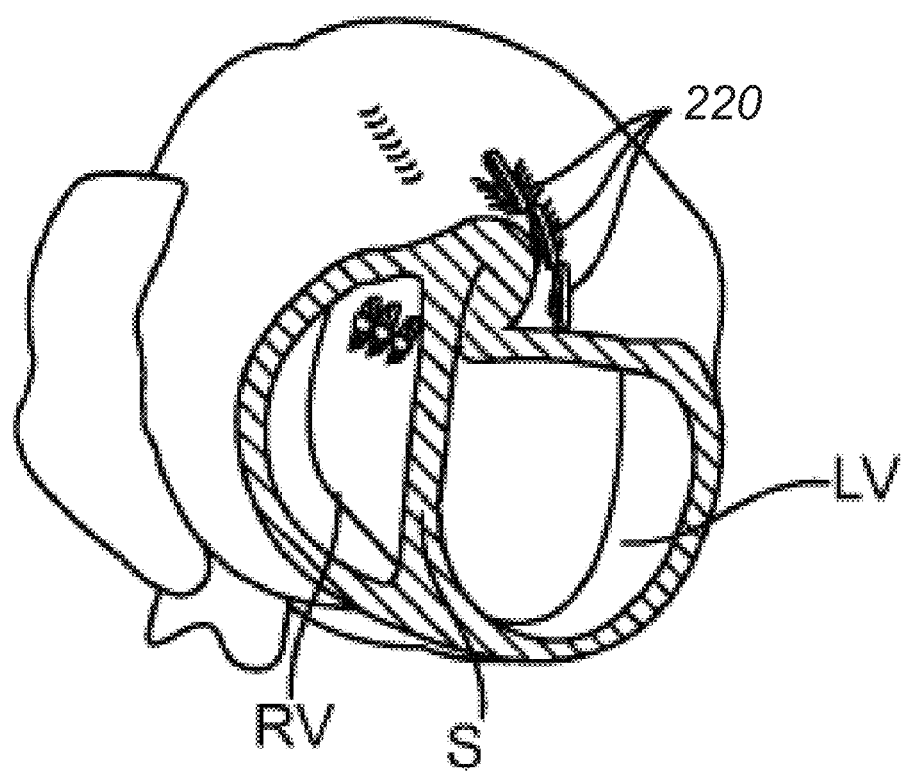

As shown in FIG. 5G, the procedure can be repeated a number of times with other sets of epicardial anchors 220 and septal anchors 222 being deployed along a pre-selected apposition line. The sets of epicardial anchors 220 and septal anchors 222 may be tightened to produce a cinching effect of the left ventricle LV, reducing its volume. Different sets of epicardial anchors 220 and septal anchors 222 may be alternately tightened as desired. A cutter (not shown) may then be advanced adjacent to a locking mechanism (not shown) to cut an unused portion of tether T, which may then be removed from the heart.

Figure 6:
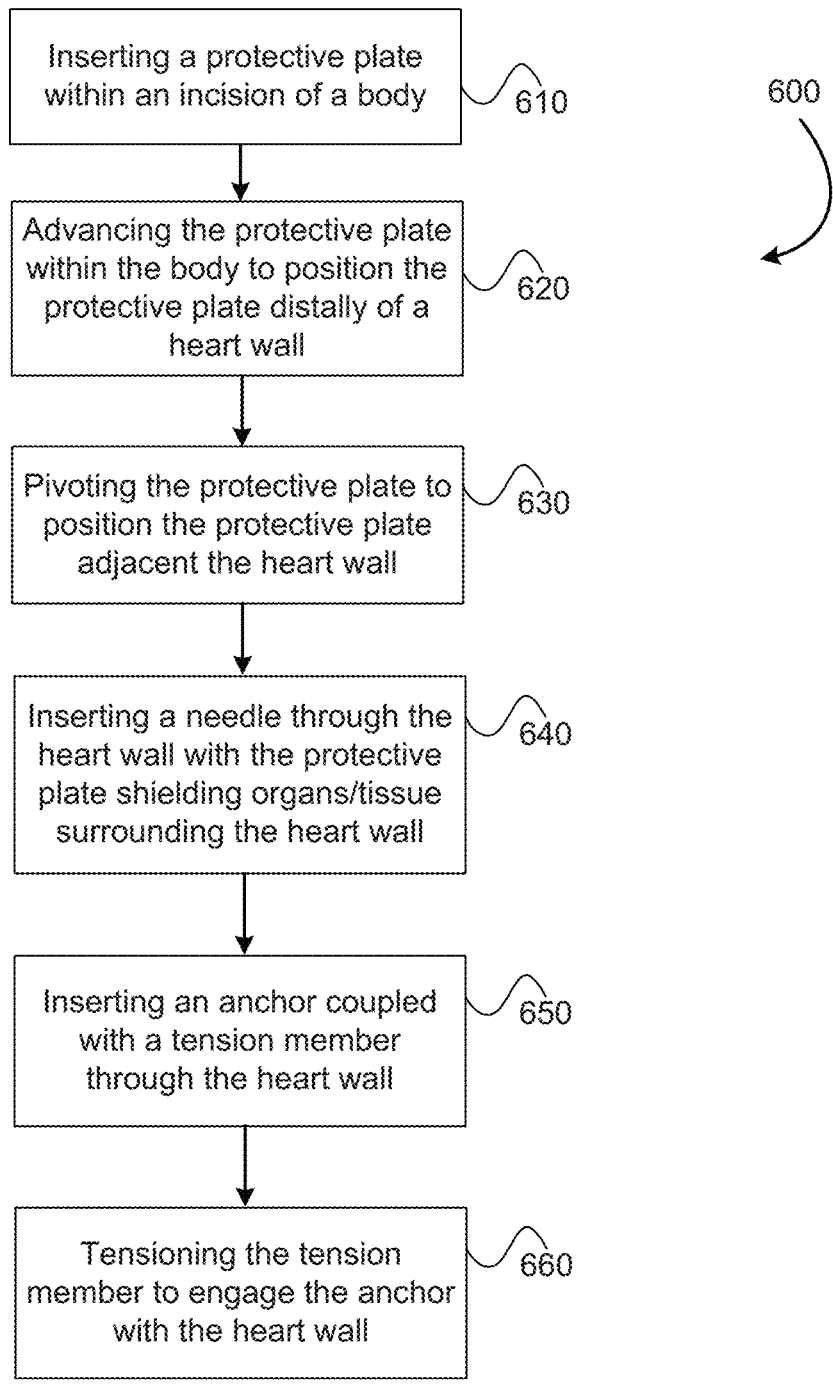
FIG. 6 illustrates a method for treating congestive heart failure.

Referring now to FIG. 6, illustrated is a method for treating congestive heart failure. At block 610, a protective plate of a protective device is inserted within an incision of a body. The protective plate is pivotably coupled with a distal end of an elongate shaft of the protective device. The elongate shaft allows the protective plate to be inserted and navigated within the body while a control mechanism of the protective device is positioned outside the body. At block 620, the protective plate is advanced or navigated within the body to position the protective plate distally of a rear wall of a heart. As described herein, the rear wall of the heart may be a left ventricular wall or right ventricular wall. In some embodiments, the protective plate may be inserted within an incision of the front of the patient's body (e.g., through or adjacent the chest) and the rear wall of the heart may be adjacent the patient's back.

At block 630, the control mechanism is operated to pivot the protective plate relative to the elongate shaft in order to position the protective plate adjacent the rear wall of the heart. The protective plate may be pivoted from a first position, in which a body of the protective plate is roughly aligned with an axis of the elongate shaft, to a second position, in which the body of the protective pate is angled relative to the axis of the elongate shaft. In some embodiments, the protective plate may be incrementally pivoted between the first and second positions. The control mechanism may be coupled with a proximal end of the elongate shaft. In some embodiments, the control mechanism may include a lock mechanism and the method may also include actuating the lock mechanism to lock the protective plate in the second position.

In some embodiments, operating the control mechanism is performed by actuating a trigger mechanism that is configured to pivot the protective plate to position the protective plate adjacent the rear wall. Actuating the trigger mechanism may cause an inner or actuating shaft that is disposed within a lumen of the elongate shaft to slide within the elongate shaft's lumen and thereby pivot the protective plate. In some embodiments, the control mechanism may be operated or actuated to pivot the protective plate while the protective plate is advanced distally of the rear wall. In such embodiments, the protective plate is pivoted into position adjacent the rear wall during advancement or navigation of the protective plate distally of the rear wall so that pivoting and advancement occur essentially simultaneously or close in time. In some embodiments, the protective plate is positioned behind an apical portion of the heart. The protective plate may have an arcuate configuration that aids in positioning the protective plate behind the apical portion of the heart.

At block 640, a needle is inserted through the rear wall of the heart. The protective plate is positioned between the needle and body organs or tissue surrounding the rear wall to shield the body organs or tissue from being damaged by the needle during insertion of the needle through the rear wall or subsequent thereto. At block 650, an anchor is inserted through the rear wall of the heart. The anchor is coupled at a distal end of a tension member that extends through the rear wall of the heart. At block 660, the tension member is tensioned to engage the anchor with the rear wall and urge the rear wall toward another wall of the heart.

In some embodiments, the method may further include positioning an additional anchor adjacent an additional wall of the heart. The additional anchor may be slidable along the tension member and couplable therewith. Tensioning of the tension member may engage the additional anchor with the additional wall and urge the rear wall and the additional wall toward one another. The method may additionally include locking the additional anchor to the tension member with the additional anchor engaged with the additional wall and the anchor engaged with the rear wall.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A tissue protecting device for use in treatment of congestive heart failure comprising:
   a control mechanism;
   an elongate shaft having a proximal end and a distal end, the proximal end being coupled with the control mechanism and the elongate shaft being insertable within a body so that the distal end of the elongate shaft is advancable distally of a front wall of the heart while the control mechanism is positioned outside of the body; and
   a protective plate pivotably coupled with the distal end of the elongate shaft, the protective plate being advancable distally of a rear wall of the heart, wherein operation of the control mechanism pivots the protective plate so as to position the protective plate adjacent the rear wall of the heart to shield body organs or tissue surrounding the rear wall from being damaged by surgical instruments inserted through the rear wall;
   wherein the protective plate is substantially wider than the elongate shaft, and wherein the protective plate has a material body that extends continuously across a width of the protective plate at a center of the protective plate so as to prevent the surgical instruments from being advanced distally of the protective plate.

2. The device of claim 1, wherein the protective plate is pivotable from a first position in which the material body of the protective plate is roughly aligned with an axis of the elongate shaft to a second position in which the material body of the protective plate is angled relative to the axis of the elongate shaft.

3. The device of claim 2, wherein the control mechanism includes a locking mechanism that locks the material body of the protective plate in the second position.

4. The device of claim 1, wherein the protective plate has an arcuate configuration.

5. The device of claim 1, wherein the control mechanism has a main body that is aligned according to a first plane, and wherein the protective plate is aligned according to a second plane that is roughly aligned with the first plane such that the protective plate and the control mechanism are roughly aligned on opposite ends of the elongate shaft.

6. The device of claim 1, wherein the control mechanism comprises a handle and trigger mechanism that is configured to pivot the protective plate to position the protective plate adjacent the rear wall.

7. The device of claim 1, further comprising an inner shaft disposed within a lumen of the elongate shaft, the inner shaft having a proximal end coupled with the control mechanism and a distal end coupled with the protective plate, wherein the inner shaft is configured to pivot the protective plate by sliding within the lumen of the elongate shaft upon operation of the control mechanism.

8. The device of claim 1, wherein the protective plate is positionable around an apical portion of the heart.

9. A tissue protecting device comprising:
an elongate shaft having a proximal end and a distal end, the elongate shaft being insertable within a body so that the distal end of the elongate shaft is advancable toward a wall of a heart while the proximal end is positioned outside of the body;
a protective element coupled with the distal end of the elongate shaft, the protective element being positionable adjacent the heart wall to shield body organs or tissue surrounding the heart wall from being damaged by surgical components inserted through the heart wall; and
a control mechanism coupled with the proximal end of the elongate shaft, wherein operation of the control mechanism pivots the protective element relative to the elongate shaft;
wherein the protective element is wider than the elongate shaft, wherein the protective element has a unitary body that extends across a center of the protective element so as to prevent the surgical components from being advanced distally of the protective element, wherein the unitary body forms a protective plate of the protective element, and wherein the unitary body is relatively wide and arcuate.

10. The device of claim 9, wherein the protective element is pivotable relative to the elongate shaft from a first position in which the protective element is roughly aligned with an axis of the elongate shaft to a second position in which the protective element is angled relative to the axis of the elongate shaft.

11. The device of claim 10, wherein the control mechanism is configured to pivot the protective element from the first position to the second position.

12. The device of claim 11, wherein the control mechanism includes a locking mechanism that locks the protective element in the second position.

13. The device of claim 11, wherein the control mechanism and the protective element are roughly aligned on opposite ends of the elongate shaft.

14. The device of claim 11, wherein the control mechanism comprises a handle and trigger mechanism that is configured to pivot the protective element from the first position to the second position.

15. The device of claim 10, further comprising an inner shaft disposed within a lumen of the elongate shaft, the inner shaft being configured to pivot the protective element from the first position to the second position by sliding within the lumen of the elongate shaft.

* * * * *